(12) United States Patent
Chen et al.

(10) Patent No.: US 9,549,872 B2
(45) Date of Patent: Jan. 24, 2017

(54) CHRONIC ELECTROACCUPUNCTURE USING IMPLANTED ELECTRODES

(71) Applicants: Jiande Chen, Houston, TX (US); Jieyun Yin, League City, TX (US)

(72) Inventors: Jiande Chen, Houston, TX (US); Jieyun Yin, League City, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 13/967,398

(22) Filed: Aug. 15, 2013

(65) Prior Publication Data

US 2014/0051906 A1 Feb. 20, 2014

Related U.S. Application Data

(60) Provisional application No. 61/683,449, filed on Aug. 15, 2012.

(51) Int. Cl.
| | |
|---|---|
| *A61N 1/18* | (2006.01) |
| *A61H 39/00* | (2006.01) |
| *A61F 5/00* | (2006.01) |
| *A61N 1/36* | (2006.01) |
| *A61N 5/02* | (2006.01) |

(52) U.S. Cl.
CPC ............ *A61H 39/002* (2013.01); *A61F 5/0026* (2013.01); *A61N 1/3606* (2013.01); *A61N 1/36146* (2013.01); *A61N 1/36007* (2013.01); *A61N 1/36085* (2013.01); *A61N 1/36153* (2013.01); *A61N 1/36157* (2013.01); *A61N 1/36171* (2013.01); *A61N 1/36175* (2013.01); *A61N 1/36178* (2013.01); *A61N 5/022* (2013.01)

(58) Field of Classification Search
CPC ............ A61N 1/36085; A61N 1/36082; A61N 1/3606; A61H 39/002; A61F 5/0026
USPC ...................................... 607/40, 133
See application file for complete search history.

(56) References Cited

U.S. PATENT DOCUMENTS

| | | | |
|---|---|---|---|
| 4,621,642 A * | 11/1986 | Chen ........................ | A61N 5/04 607/76 |
| 5,211,175 A | 5/1993 | Gleason | |
| 2003/0187483 A1* | 10/2003 | Grey et al. ...................... | 607/40 |
| 2004/0049240 A1 | 3/2004 | Gerber | |
| 2008/0015642 A1 | 1/2008 | Johnson | |

(Continued)

OTHER PUBLICATIONS

Diehl, David L. Acupuncture for Gastrointestinal and Hepatobiliary Disorders. 1999. The Journal of Alternative and Complimentary Medicine. vol. 5, No. 1. p. 27-45.*

(Continued)

*Primary Examiner* — Christopher D Koharski
*Assistant Examiner* — Michael Carey
(74) *Attorney, Agent, or Firm* — Norton Rose Fulbright US LLP

(57) ABSTRACT

Certain embodiments are directed to methods of treating a metabolic disease in a subject using a fully implantable electrical stimulation system to provide or administer a therapy. In certain aspects a stimulation lead is implanted proximally to a stomach acupoint, the stimulation lead being coupled to an implantable signal generator; and stimulating the acupoints using the signal generator to treat the metabolic disease.

18 Claims, 8 Drawing Sheets

(56) References Cited

U.S. PATENT DOCUMENTS

| | | | | |
|---|---|---|---|---|
| 2008/0249587 | A1* | 10/2008 | Cho | A61H 39/002 |
| | | | | 607/46 |
| 2010/0228313 | A1* | 9/2010 | Starkebaum et al. | 607/40 |
| 2013/0131753 | A1* | 5/2013 | Simon | A61N 1/36007 |
| | | | | 607/40 |
| 2014/0214124 | A1* | 7/2014 | Greiner | A61N 1/36114 |
| | | | | 607/59 |

OTHER PUBLICATIONS

Wang, Fei, et al. "Electroacupuncture in the Treatment of Obesity." Aug. 22, 2008. Neurochemical Research. vol. 33. pp. 2023-2027.*

Chen, J. Effects and Mechanisms of Chronic Electroacupuncture for Emesis, NIH grant application abstract, project 5R21CA14995602 (2011).

Chen, J. Transcutaneous Electroacupuncture for Gastroparesis, NIH grant application abstract, project 5R43AT00448902. (2010).

Teng et al., Biological Effects of Microwaves in Accupuncture, Microwaves Laboratory U.C.L, Maxwell Building B-1348 Louvain-La-Neuve, Belgium, 918-923. (1989).

Yin, et al. Ameliorating effects and mechanisms of electroacupuncture on gastric dysrhythmia, delayed emptying, and impaired accommodation in diabetic rats. Am J Physiol Gastrointest Liver Physiol 298 (2010).

Yin, J., Chen, J. Electroacupuncture improves rectal distension-induced delay in solid gastric emptying in dogs. Am J Physiol Regul Integr Comp Physiol 301. 2011.

* cited by examiner

CHRONIC ELECTROACCUPUNCTURE USING IMPLANTED ELECTRODES

PRIORITY CLAIM

This application is a non-provisional application of and claims priority to U.S. Provisional Application Ser. No. 61/683,449 filed Aug. 15, 2012, which is incorporated herein by reference in its entirety.

STATEMENT REGARDING FEDERALLY FUNDED RESEARCH

This invention was made with government support under CA14995602 awarded by the National Institutes of Health. The government has certain rights in the invention.

BACKGROUND

In the United States, a majority of the population is overweight or obese. People who are overweight or obese are generally more prone to ailments such as high blood pressure, heart disease, stroke, and diabetes.

To lose weight and combat the conditions associated with excess weight, many individuals partake in numerous methods and/or procedures to lose weight. For example, individuals attempt diets, undertake exercise routines or regimens, purchase and use weight reduction equipment or weight reduction drugs, and the like.

Acupuncture has long been used to treat anxiety, back pain, high blood pressure, and osteoarthritis. People are now turning to acupuncture as a treatment for weight loss. Acupuncture is the ancient Chinese art of inserting fine needles under the surface of the skin into specific locations on the body to treat ailments and the like.

Typically, acupuncture involves the insertion of flexible, filiform needles into the skin of a patient at specific regions known as acupoints and at depths sufficient to penetrate certain tissues, musculature or the like. Subsequent manipulation of the needle ends that protrude from the skin (e.g., by manual twisting or vibration) stimulates the subcutaneous tissue and/or intramuscular sensory nerves of the patient.

Electroacupuncture is one variation of traditional acupuncture in which needles are temporarily inserted at specific acupoints along the body and then attached with clips to a device that generates electric pulses. The introduction of a mild current through the needles acts as a stimulus on the tissue and/or nerves in the vicinity of the needle.

Although electroacupuncture using implantable electrodes and an external pulse generator for acute treatment is known, there remains a need for a chronic or permanent means of providing stimulation to the acupoints or meridians.

SUMMARY

In both traditional acupuncture and electroacupuncture (EA), needles are typically inserted into acupoints temporarily and removed after each application. In certain embodiments described herein, stimulation leads or electrodes are placed at acupoints chronically or permanently. An acupoint is a location on the body that is the focus of acupuncture or acupressure. Several hundred acupoints are considered to be located along meridians (connected points across the anatomy which affect a specific organ or other part of the body). In certain aspects, the electrodes are fine needles embedded under the skin at appropriate locations.

The term "chronically" refers to provision or administration of a therapy or device for durations exceeding about 24 hours with the expectation that the therapy will continue or the device will remain implanted for days, weeks, or months. The term "permanently" refers to provision or administration of a therapy or device for durations exceeding about a year with the expectation that the therapy will continue or the device will remain implanted for 1 or more years.

In one embodiment, the connecting wires of the chronically implanted stimulation leads or electrodes will be tunneled under the skin and connected to a pulse generator (stimulator), which can be chronically implanted at a location of convenience (usually in the abdomen) under the skin. In certain aspects, the connection between the electrode and stimulator will be such that the stimulator will be implanted at the acupoint. Electrical stimulation can be performed via the implanted stimulation leads or electrodes using a built-in clock and programmer, or using an external switcher, such as a magnetic switcher. Electrical stimulation can be monopolar, in which case the implanted pulse generator will serve as one electrode, or bipolar in which case two electrodes placed at two different acupoints will form a circuit. Multiple-channel stimulation is also possible with the use of multiple stimulation leads or electrodes at different acupoints.

In another embodiment, the implanted stimulation leads or electrodes are able to receive a remote signal from an external device. In this case, only the stimulation leads or electrodes will be permanently implanted. Electrical stimulation can be performed using an external device that is placed on the skin surface of the implanted stimulation lead or electrode. An external stimulator is capable of coupling stimulation pulses it generates to implanted stimulation leads or electrodes and thereby delivering electrical current to the acupoints.

In another embodiment, the implanted stimulation leads or electrodes will serve as an object that receives magnetic field or microwave signals from an external device. The external device will generate microwaves or magnetic fields. The microwaves or magnetic fields generated by the external device can heat the implanted stimulation leads or electrodes to a certain degree and thereby delivering thermo-stimulation to surrounding tissues.

The above mentioned technologies can be applied for treating chronic conditions including: metabolic conditions such as obesity and diabetes; functional gastrointestinal diseases (such as gastroesophageal reflux, functional dyspepsia, irritable bowel syndrome); chronic gastrointestinal discomfort such as chronic constipation, chronic diarrhea, chronic pain, chronic nausea and vomiting not associated with chemotherapy; and chemotherapy-induced nausea and vomiting (CINV). In certain aspects CINV is specifically excluded.

In certain embodiments, an electrical stimulation comprises a pulse train of 0.1, 0.2, 0.3, 0.4, 0.5, 1, 2, 3, 4, 5 seconds on and 0.1, 0.2, 0.3, 0.4, 0.5, 1, 2, 3, 4, 5 seconds off with pulses of 0.1 to 1 ms, 1 to 200 Hz, and 0.1 mA to 10 mA. In certain aspects stimulation is provided for 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, weeks, months, years or longer. In certain aspects the therapy can be provided intermittently over 1 to 52 weeks, or 1, 2, 3, 4, 5, 10 or more years (including all values and ranges there between). In other aspects electrical stimulation is provided on an as needed basis or during particular periods designated by a subject, a treating physician, or other person.

Certain embodiments are directed to methods of treating a metabolic disease in a subject using a fully implantable electrical stimulation system comprising: (a) positioning a stimulation lead proximally to a stomach acupoint of Zusanli (ST 36), Liangmen (ST21), and/or Tianshu (ST25), Zhong Wan (CV4) and/or Guanyuan (CV 12); (b) coupling the stimulation lead to an implantable signal generator; and (c) generating an electrical signal with the signal generator using the stimulation lead wherein the signal electrically stimulates the subject's acupoints thereby treats the metabolic disease. In certain aspects, the metabolic disease is diabetes or obesity. In further aspects, the electrical stimulation reduces the postprandial glucose levels in the subject and/or increases insulin sensitivity in the subjects.

Certain embodiments are directed to methods of treating a functional gastrointestinal disease in a subject using a fully implantable electrical stimulation system comprising (a) positioning a stimulation lead proximally to a stomach acupoint of Zusanli (ST 36), Liangmen (ST21), and/or Tianshu (ST25), Zhong Wan (CV4) and/or Guanyuan (CV 12); (b) coupling the stimulation lead to an implantable signal generator; and (c) generating an electrical signal with the signal generator using the stimulation lead wherein the signal electrically stimulates the subject's acupoints thereby treats the functional gastrointestinal disease. In certain aspects, the functional gastrointestinal disease is gastroesophageal reflux (GERD), functional dyspepsia, chronic intestinal pseudo-obstruction, diarrhea, constipation, irritable bowel syndrome, or fecal incontinence. In a further aspect, gastroparesis is specifically excluded. In certain aspects, the acupoint is ST36 and/or PC6.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

I. Implantation of Stimulation Leads

Figure 1A:
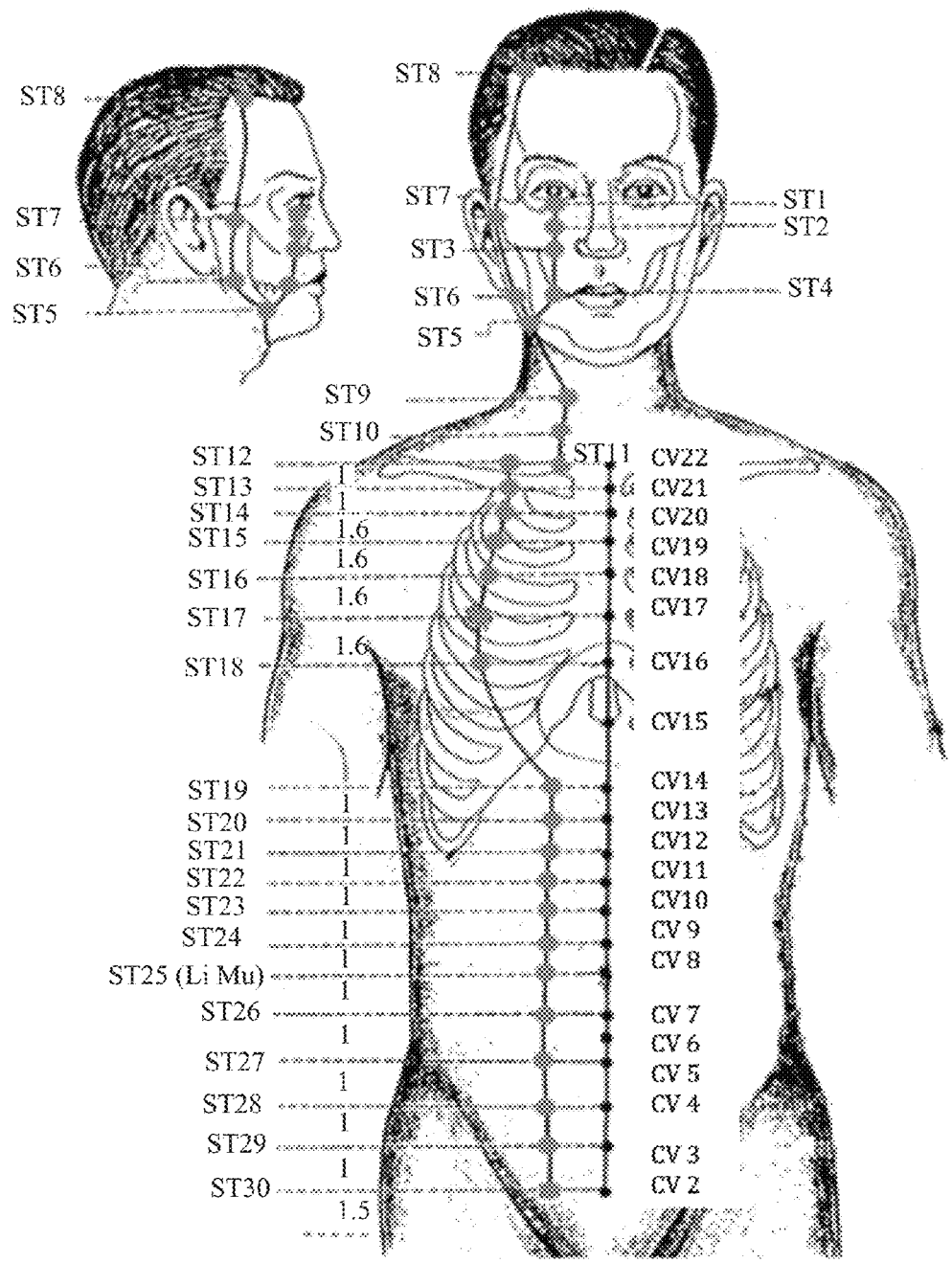
FIGS. 1A and 1B illustrate the acupuncture points (acupoints) and meridians associated with the stomach.
Figure 1B:
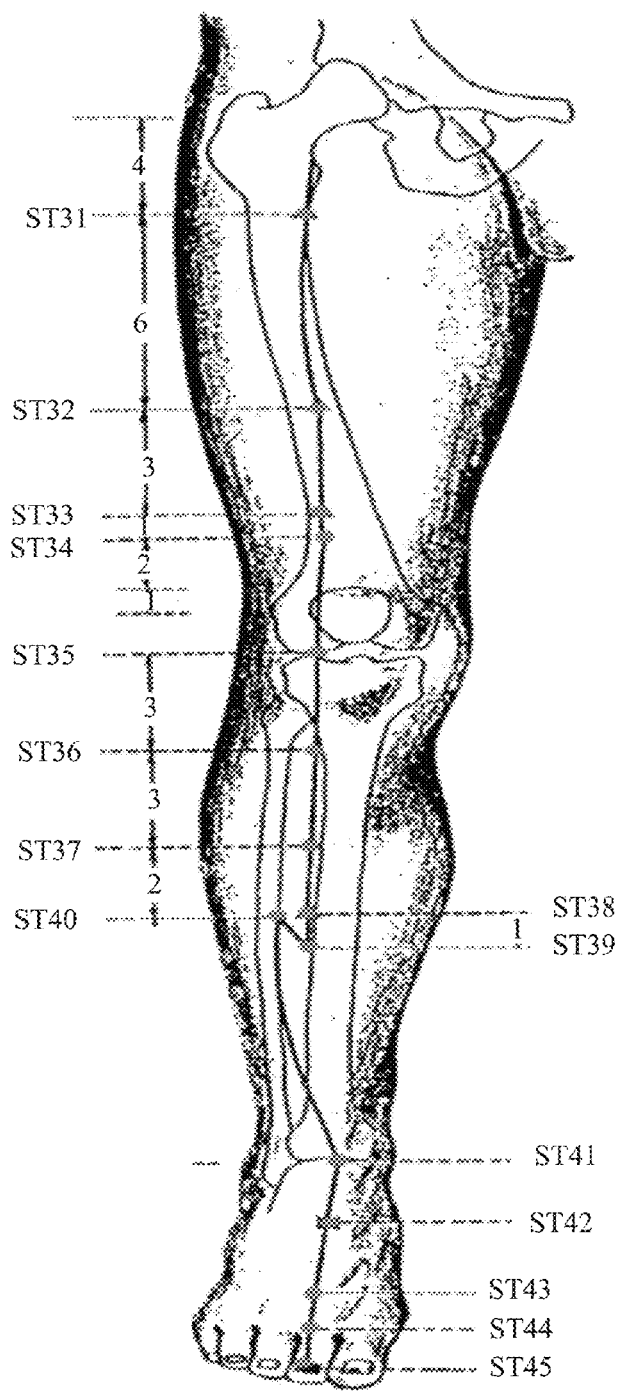

FIGS. 1A and 1B show the acupoints and meridians, as identified by Chinese acupuncture, of the stomach. There are 45 stomach acupoints (ST1-45), some of which are of more interest relating to reduction of food intake, for example, but not limited to, ST 21, ST25, and ST36. ST21 is also referred to as Liangmen (Chinese name) or Beam Gate (English name). It is located 2 cun (cun is equivalent to the width of a person's thumb or knuckle) lateral to the AML level with CV12. ST25 is also referred to as Tianshu (Chinese name) or Celestial Pivot (English name). ST25 is located 2 cun lateral to the AML level with CV 8. ST36 is also referred to as Zusanli (Chinese name) or Leg Three Li (English name). ST36 is located 3 cun below ST35, one finger width lateral from the anterior border of the tibia. Other acupoints that may be of interest include Neiguan (PC6), Guangyaun (R4), and/or Quchi (LI11).

In certain aspects, one or more stimulation leads or electrodes are positioned on or in a target tissue at a targeted acupoint, for example at ST21, ST 25, ST36, CV4, and/or CV12. In certain aspects, the stimulation leads or electrodes used herein are commercially available and can include any that are suitable for the application, such as those used with deep brain leads, percutaneous leads, paddle leads, patch electrodes, cuff electrodes, needle electrodes, etc. In certain aspects, needle electrodes or screw electrodes can be used.

Techniques for implanting stimulation leads or electrodes are well known by those of skill in the art and may be positioned in various body tissues and in contact with various tissue layers; for example, deep brain, cortical, subdural, subarachnoid, epidural, cutaneous, transcutaneous and subcutaneous implantation is employed in some embodiments.

In certain embodiments, the stimulation leads or electrodes are implanted such that they are positioned or disposed near, or in communication with a target acupoint or meridian, for example, but not limited to ST21, ST25, ST36, CV4, and/or CV12. This implantation may be subcutaneous such that the stimulation lead or electrode is below the dermis and epidermis and within the subcutaneous tissue or the implantation may be such that the stimulation lead or electrode is positioned on or above the fascia or under the fascia depending upon the desired stimulation. Furthermore, if muscular stimulation is more desirable, the stimulation leads or electrodes may be inserted into the muscle. Still further, the stimulation leads or electrodes may be inserted within the target acupoint or meridian such that the stimulation lead or electrode targets a specific nerve or nerve network within the acupoint or meridian. In certain aspects, the electrode is inserted at a depth of about 1, 2, 3, 4, 5, 6, 7, 8, 9, or 10 mm depending on location(s).

Figure 2A:
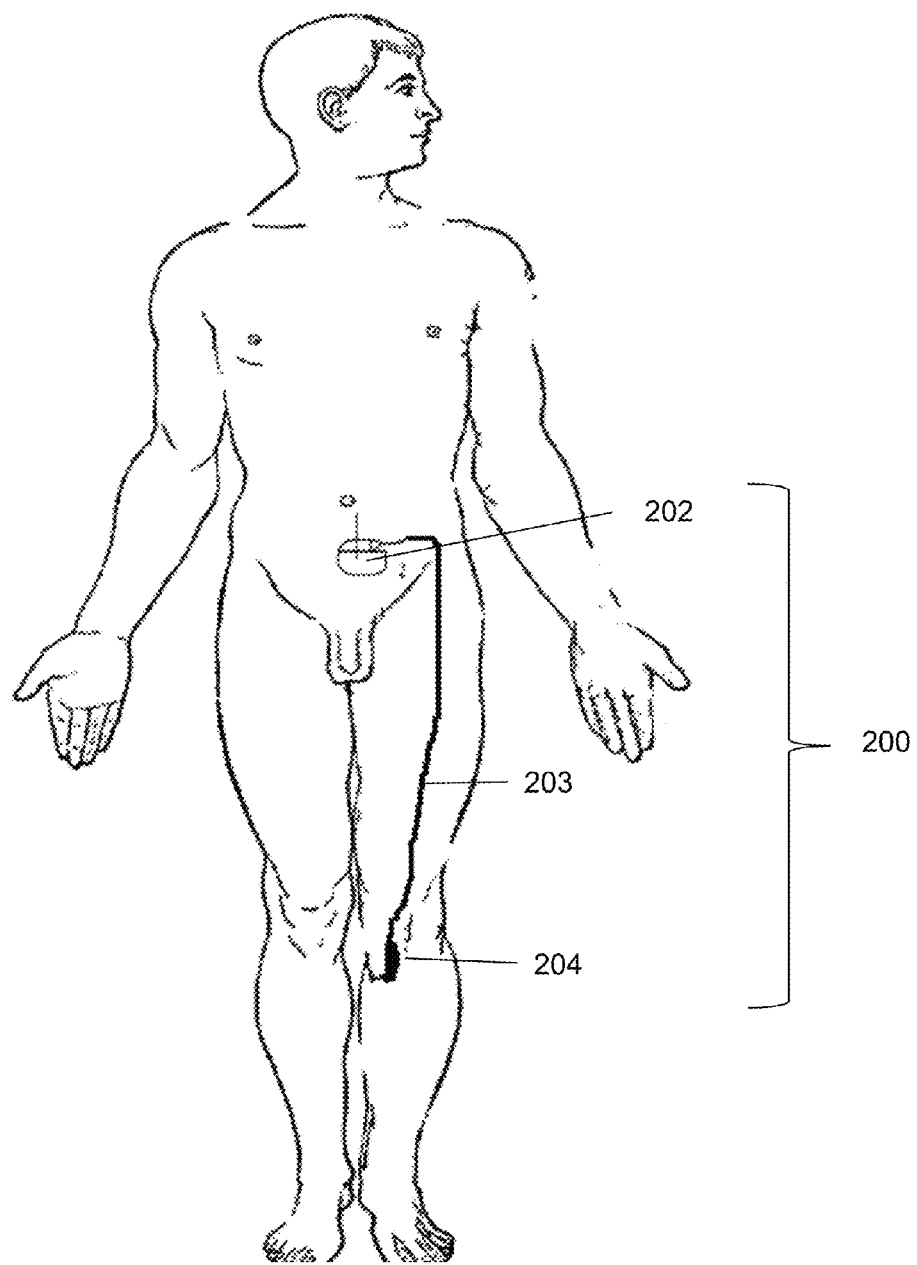
FIGS. 2A and 2B illustrate the placement of an implantable electrostimulation device.
Figure 2B:
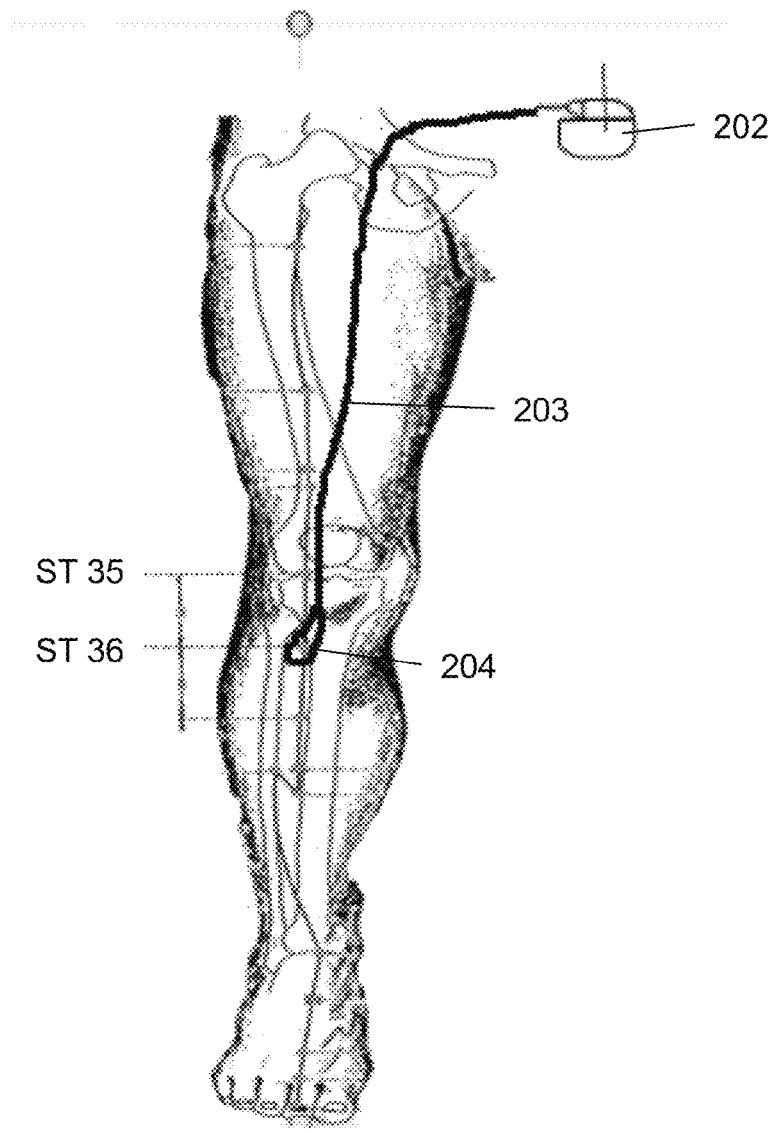

FIGS. 2A-2B illustrate example implantation of the stimulation system 200 for electrically stimulating ST36 or Zusanli acupoint or meridian to treat a chronic disorder, such obesity, diabetes, pain, gastrointestinal disorders, etc. The stimulator 202 can be implanted in the patient's abdomen. Alternatively, the stimulator 202 can be implanted in another location that the surgeon may prefer, such as the buttocks or chest. The stimulator 202 is connected to the connector 203 that further connects to at least one stimulation lead or one electrode 204 at the end distal to the stimulator 202. The stimulation lead or electrode 204 is positioned to stimulate the ST36 point. If it is necessary, suture, staples, hooks, barbs or screws, can be used to anchor the stimulation lead or electrode to improve the electric contact with the tissue. Stimulation system 200 can be programmed to generate monopolar or bipolar stimulation depending upon the desired stimulation pattern. Still further, depending upon the desired pattern of stimulation, the stimulation lead or electrode 204 may be a percutaneous lead comprising circular electrodes in which stimulation could be achieved in all directions. If the desired stimulation pattern is directional, then paddle leads or other electrodes that provide a directional stimulation may be used. In the case of monopolar stimulation, the stimulator itself may serve as an electrode.

In general terms, the stimulation system 200 includes: (1) a stimulator 202 that can be an implantable pulse generating source or electrical stimulation source, and (2) one or more stimulation leads or electrodes 204 for stimulating the target site. In operation, both of these primary components are implanted in the person's body, as discussed below. In certain embodiments, stimulator 202 is coupled to a stimulation lead or electrode 204 via a connector 203. In certain other embodiments, stimulator 202 is directly coupled to stimulation lead or electrode 204. For example, such a stimulation system 200 may be a Bion® stimulation system manufactured by Advanced Bionics Corporation. Whether stimulator 202 is coupled directly or indirectly to stimulation lead or electrode 204, stimulator 202 controls the stimulation transmitted to one or more stimulation leads or electrodes 204 that is positioned at or in communication with a target site. A health professional, the patient, or another user of stimulator 202 may directly or indirectly input stimulation parameters to specify or modify the nature of the stimulation provided.

Stimulator 202 can include an implantable pulse generator (IPG). In other embodiments, the stimulator 202 may include an implantable wireless receiver. The wireless receiver is capable of receiving wireless signals from a wireless transmitter located external to the person's body. A health professional, the patient, or another user of stimulator 202 may use a controller located external to the person's body to provide control signals for operation of stimulator 202. The controller provides the control signals to wireless transmitter, which transmits the control signals and power to the wireless receiver of stimulator 202, and stimulator 202 uses the control signals to vary the stimulation parameters transmitted through stimulation lead or electrode 204. Thus, the external controller can be for example, a handheld programmer, to provide for programming the IPG.

Figure 3:
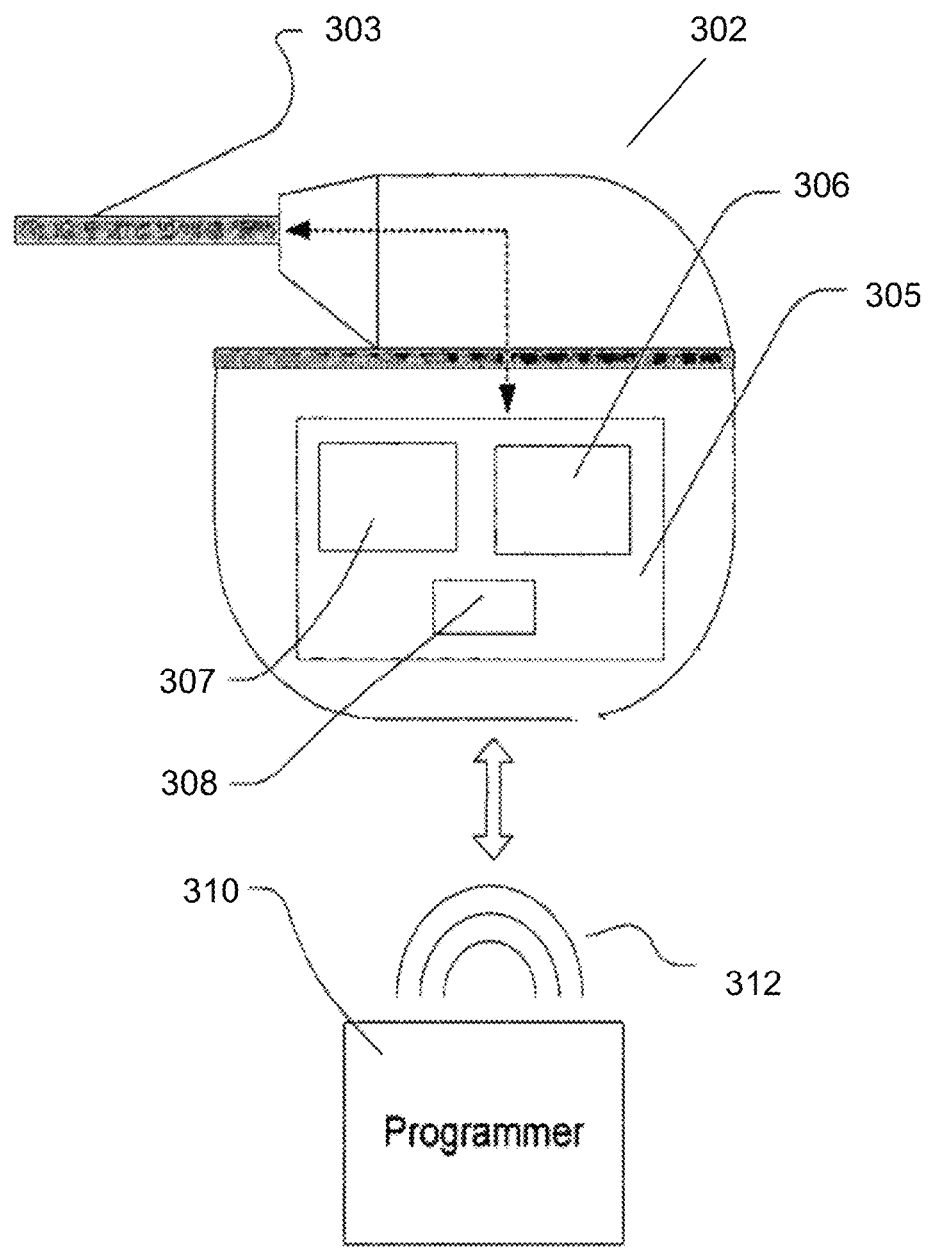
FIG. 3 provides a design of a general implantable pulse generator.

FIG. 3 provides a schematic of the basic design of stimulator 302, e.g., an implantable pulse generator (IPG). Stimulator 302 is typically enclosed in a titanium case. Electronic circuitry 305 is housed inside the case and usually includes a battery 307, a microprocessor 306, and a programming interface 308. Programming of the stimulator can be achieved using traditional radio frequency (RF) communication 312. The blue tooth technology may also be used to program the implanted stimulator or electrodes. The programmer 310 is an external device to interrogate the microprocessor, collect information, and change the stimulation parameters. Any suitable commercially available stimulator can be modified according to the embodiments as described herein, such commercially available stimulators include the Eon® or Eon Mini® manufactured by St. Jude Medical systems (Plano, Tex.) and Synergy® manufactured by Medtronic, Inc. (Minneapolis, Minn.). These stimulators are fully implantable, externally programmable, and operate a variety of implantable leads and electrodes that are adapted for chronic or permanent implantation in the body.

Figure 4:
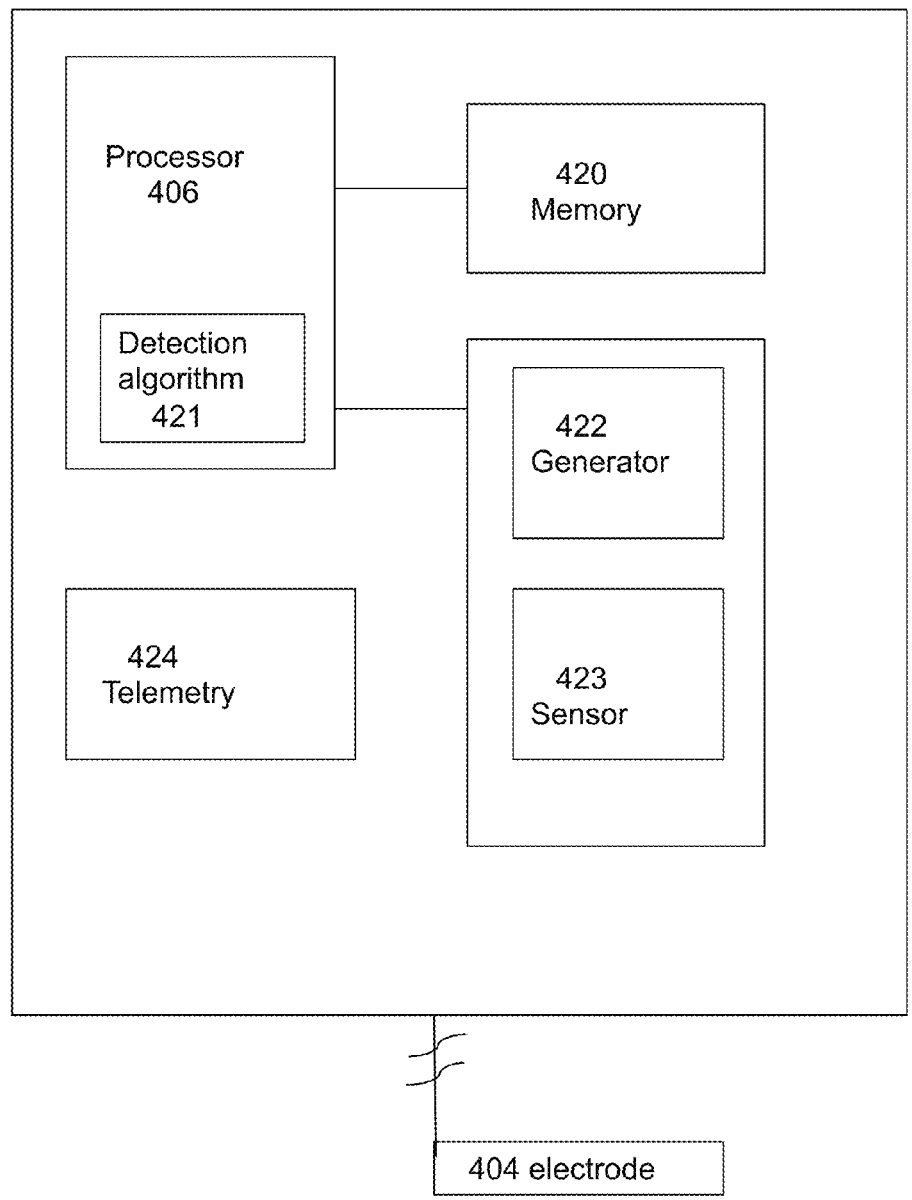
FIG. 4 provides an illustration of an implantable device that can be used to synchronize the stimulation.

FIG. 4 shows an example of an implantable device that can be used to determine a breathing frequency and adjust therapy or administer therapy. For example, the device may include, processor 406, memory 420, generator 422, sensing module 423, telemetry module 424, and HRV (heart rate variable) algorithm module 421. Although HRV module 421 is shown to be a part of processor 406 in FIG. 4, in other examples, HRV module 421 and processor 406 may be separate components and may be electrically coupled, e.g., via a wired or wireless connection.

Figure 5:
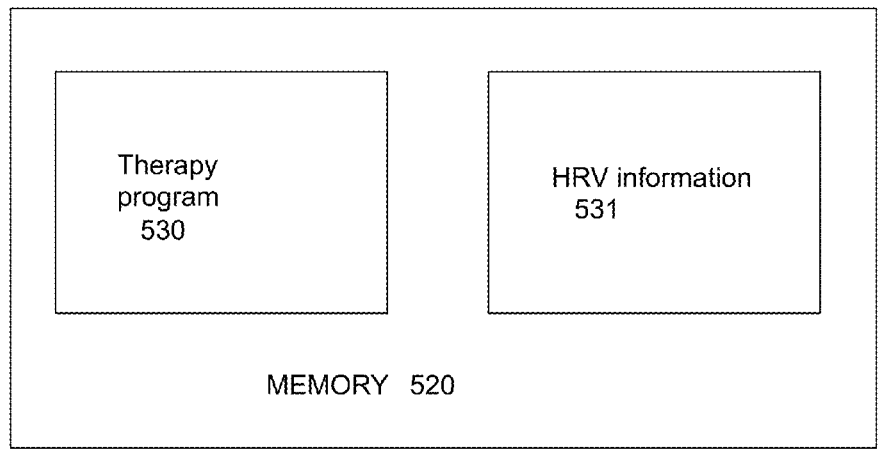
FIG. 5 provides an illustration of memory in which multiple programs are employed.

Memory 520, as shown in FIG. 5, may include any volatile or non-volatile media, such as a random access memory (RAM), read only memory (ROM), non-volatile RAM (NVRAM), electrically erasable programmable ROM (EEPROM), flash memory, and the like. Memory 520 may store instructions for execution by processor 306 or 406 (FIGS. 3 and 4 respectively) and information defining therapy delivery for the patient, such as, but not limited to, therapy programs or therapy program groups, information associating therapy programs with breathing rates, thresholds or other information used to detect breathing rates based on biosignals (such as heart rate variability or detection of R-R intervals (i.e., the interval from the peak of one QRS complex to the peak of the next as shown on an electrocardiogram; it is used to assess the ventricular rate), and any other information regarding therapy of the patient. Therapy information may be recorded in memory 520 for long-term storage and for retrieval by a user. As described in further detail with reference to FIG. 5, memory 520 may include separate memories for storing information, such as separate memories for therapy programs 530, and breathing rate or HRV information 531. In certain aspect, other information can be stored such as patient information.

In addition to electrical stimulation, other forms of stimulation can be used, for example magnetic or microwaves. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. It is envisioned that the microwaves or magnetic field generated by the external device will heat the implanted leads and provide thermal stimulation to the tissues.

Synchronized Electroacupuncture. In certain embodiments the stimulation is synchronized with breathing using a paired-timing system or biofeedback. For example, the subject synchronizes or uses a system to synchronize breathing according to the stimulation frequency of the pulse generator to increase vagal activity. Furthermore, it may be of interest to use a stimulation system that includes a processor that determines the patient's breathing frequency such that the stimulation can be synchronized with the patient's breathing or heart rate. The synchronization may occur with either the stimulation or the biological activity as the driver (independent variable). In other words, the stimulation may be prompted by the detection of breathing frequency or heart rate. Alternatively, the patient may be instructed to inhale or exhale in response to detecting stimulation. In certain aspects the stimulatory signals are synchronized to the breathing. In other aspects, the breathing is synchronized to the stimulatory signals.

Figure 6:
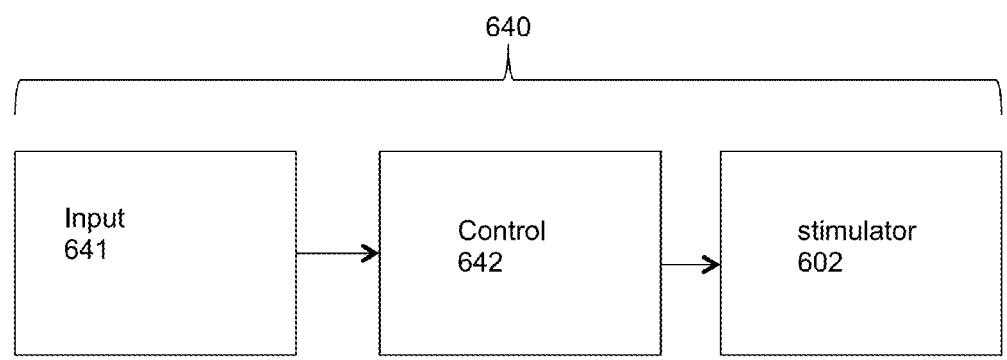
FIG. 6 provides an illustration of a synchronized training system.

With reference to FIG. 6, the synchronized stimulation system 640 comprises a sensor 641, a timing control system 642 and the stimulation system 602. The timing control system 642 generally provides the simultaneous nature of the pairing. The stimulation and the trigger are simultaneous in that they occur at the same time, that is, there is at least some overlap in the timing. In some embodiments, the stimulation may lead the start of the trigger, while in other embodiments the stimulation may follow the start of the trigger. In many cases, the stimulation is shorter in duration than the trigger, such that the stimulation occurs near the beginning of the trigger. The control system 642 can be manual or included in a closed loop type system. In a manual control system, the control 642 receives timing instructions from a manual input 641 and provides timing instructions to the stimulation system 602, so that the stimulation and trigger occur simultaneously.

In a closed loop timing control system, the closed loop timing control system includes control system 642 that receives timing instructions from the sensor (see sensor 423 of FIG. 4) (such as an ECG sensor) and provides timing instructions to the stimulation system 602, so that the stimulation and trigger occur simultaneously.

In certain embodiments the timing controller 642 may comprise an ECG amplifier and software algorithm to derive heart rate variability (HRV) from ECG and to calculate power spectrum of the HRV signal.

II. Methods to Treat Gastrointestinal Conditions and/or Eating Disorders

Embodiments herein provide a novel method of treating gastrointestinal conditions and/or eating disorders by stimulating tissue associated with the stomach meridians or acupoints, for example, but not limited to ST21, ST25, and/or ST36. Other acupoints that may be stimulated include, but are not limited to, Neiguan (PC6), Guangyaun (R4), and/or Quchi (LI11).

Certain embodiments of the present invention involve a method of treating a gastrointestinal disorder comprising the steps of: surgically implanting a stimulation lead or electrode having a proximal end and a stimulation portion, wherein after implantation the stimulation portion is in communication with a predetermined site; coupling the proximal end of the stimulation lead or electrode to a signal generator; and generating a signal with the signal generator to modulate the predetermined site thereby treating the chronic disorder, such as obesity, diabetes, functional gastrointestinal diseases (e.g., gastroesophageal reflux, functional dyspepsia, irritable bowel syndrome, constipation and chronic diarrhea), chronic pain, chronic nausea and vomiting, and/or chemotherapy-induced emesis. The predetermined sites include, but are not limited to, the stomach acupoints and associated meridian(s) that are known by those of skill in the art, more particularly, ST21, ST25, ST36, Neiguan (PC6), Guangyaun (R4), and/or Quchi (LI11).

The gastrointestinal disorders or conditions contemplated by the present invention include gastrointestinal altered motility, sensitivity and secretion disorders in which one or more of the symptoms and conditions affect the gastrointestinal tract from the mouth to the anus. Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, menstrual cramps, pancreatitis, spastic and interstitial cystitis and ulcers and the visceral pain associated therewith. One with skill in the art is aware that any functional gastrointestinal disorder, including but not limited to those associated with gastric motility, is appropriate for treatment with the method described herein.

The present invention is also appropriate for treating a variety of eating disorders and conditions, including compulsive eating, anorexia nervosa, and bulimia nervosa. For example, it is contemplated that the method of stimulation as described may be used to treat a patient for obesity, binge eating, or compulsive overeating. A stimulator as described herein can be implanted in the patient. The stimulator may be turned "on," thus activating the electrical stimulation to the appropriate tissue, by the patient when feelings of hunger are present. Alternatively, it is contemplated that the patient may use the stimulation in a continuous manner. Still further, an external handheld device (a "patient programmer") can be used by the patient to wirelessly communicate with the implanted stimulator system to initiate the electrical stimulation at an appropriate time. Thus, in a treatment of obesity, the stimulation reduces food intake and/or increases satiety.

Still further, a reduction in a subject's body mass index (BMI) can be used as an indicator of reduction of food intake or as a treatment of obesity. BMI is calculated as body weight per height in meters squared ($kg/m^2$). "Obesity" refers to a condition whereby an otherwise healthy subject has a BMI greater than or equal to 27 or 30 $kg/m^2$ (per the definition of obesity in some Asian countries and the USA, respectively), or a condition whereby a subject with at least one obesity-related disease has a BMI greater than or equal to 27 $kg/m^2$. A BMI of about 27 $kg/m^2$ is considered to be in the 85th percentile for BMI. Thus, a subject that is greater than or equal to the 85th percentile for BMI can be considered obese.

The use of a stimulation method may further mediate orexigenic/anorexigenic hormones thereby involving the reward system via the dopaminergic pathways. For example, it is known that anorexigenic/orexigenic hormones play a role in food intake, and these hormone levels are altered by electroacupuncture. Thus, stimulation of the stomach meridian points may alter the levels of ghrelin, neuropeptide Y, cholecystokinin (CCK), polypeptide Y (PYY). For example, stimulation will reduce orexigenic hormones, such as ghrelin and NPY, and increase anorexigenic hormones, such as CCK and PYY. Furthermore, stimulation of the stomach acupoints may help restore balance to the dopamine system.

Yet further, the stimulation method provided herein is administered to a subject having or at high risk of having diabetes mellitus. Thus, it is envisioned that the method of stimulating a preferred acupoint or meridian may be used to reduce or ameliorate the causes or symptoms of diabetes mellitus. The stimulation can modulate at least one symptom of diabetes mellitus, for example, decrease blood glucose or modulate blood insulin levels.

Risk factors for type I diabetes include islet-cell antibodies. Risk factors for type 2 or gestational diabetes include inactivity, obesity, siblings with diabetes, and history of diabetes during pregnancy. One of skill in the art can determine the patients who would potentially benefit from a therapeutic stimulation to reduce circulating glucose levels.

In one embodiment, the stimulation is administered in an effective amount to decrease, reduce, inhibit or abrogate high glucose, or to reduce total body weight, glycosylated hemoglobin (HbA1c), or blood pressure or to modulate (positively or negatively) blood insulin levels. In the case of a diabetic condition, successful reduction of hyperglycemia may be manifested by the fasting plasma glucose level falling below 126 mg/dL, the 2-hour plasma glucose level during an oral glucose tolerance test (OGTT) falling below 200 mg/dL, or a random plasma glucose determination reading below 200 mg/dL in a symptomatic individual. In the case of a pre-diabetic condition, a successful reduction of hyperglycemia by may be manifested by the fasting plasma glucose falling below 110 mg/dL and/or the 2-hour plasma glucose on the OGTT falling below between 140 mg/dL.

Glycohemoglobin (or glycosylated hemoglobin) is measured to monitor or accurately record blood glucose levels, and it is not influenced by acute changes in blood glucose or by the interval since the last meal. Glycohemoglobin is formed when glucose reacts non-enzymatically with the hemoglobin A molecule and is composed of several fractions, the major one being HbA1c. Total glycohemoglobin (HbA1) and HbA1c (expressed as the percentage of total hemoglobin) vary in proportion to the average level of glucose over the lifespan of the red blood cell (RBC), thereby providing an index of glycemic control.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known efficacy and toxicity (if any) of the therapeutic regimens.

The therapeutic system is surgically implanted in the predetermined sites as described in the above sections. One of skill in the art is cognizant that a variety of electrodes or electrical stimulation leads may be utilized in the present invention. It is desirable to use an electrode or lead that contacts or conforms to the target site for optimal delivery of electrical stimulation.

According to one embodiment, the target site is stimulated using stimulation parameters such as, pulse width of about 0.1, 1, 10, 50, 100, 200, or 300 to about 200, 300, 400, or 500 microseconds. In one embodiment, the pulse width is about 1, 10, 20, 30, 40, or 50 to about 50, 60, 70, 80, or 90 microseconds. The frequency can be about 1, 10, 20, 30, 40, 50 to about 20, 30, 40, 50, 100, 200 Hz, or about 1, 25, 50, 75, 100, or 125 to about 100, 125, 150, 175, or 200 Hz. The voltage can be about 0.5, 1, 2, 3, 4, or 5 to about 4, 5, 6, 7, 8, 9, or 10 volts, or about 1 to about 10 volts. It is known in the art that the range for the stimulation parameters may be greater or smaller depending on the particular patient needs and can be determined by the health professional. In other aspects, the stimulation can be in the form of pulse trains. A pulse train can include a 0.1, 0.2, 0.3, 0.4, 0.5, 1, 2, 3, 4, or 5 second on period (including all values and ranges there between) and a 0.1, 0.2, 0.3, 0.4, 0.5, 1, 2, 3, 4, or 5 second off period of 0.1, 0.2, 0.3, 0.4, 0.5, 0.6, 0.7, 0.8, 0.9, 1 ms (including all values and ranges there between); 1, 2, 3, 4, 5, 6, 7, 8, 9, 10, 11, 12, 13, 14, 15, 16, 17, 18, 19, 20, 50, 100, 200 Hz (including all values and ranges there between); and 0.1, 0.5, 1, 2, 3, 4, 5, 6, 7, 8, 9, 10 mA (including all values and ranges there between) pulses. In certain aspects, stimulation parameters are: train on-time of 0.1 s, off-time of 0.4 s (or any splits of 0.5 s by on-time and off-time, such as or 0.4 s-on and 0.1 s-off, 0.3 s-on and 0.2 s-off, 0.2 s-on and 0.3s-off, or 0.1 s-on and 0.4 s-off), 100 Hz, 0.1-10 mA.

Outcomes for patients treated by the methods and systems as described herein may be tested by standard stomach emptying tests, such as radioactive meal digestion, for example as described in U.S. Pat. No. 6,548,043. Gastric motility may be tested by an antro-duodenal motility study, in which a thin tube (one-eighth inch in diameter) is passed through the nose, down the esophagus, through the stomach and into the duodenum, the first part of the small intestine. Sensors in the tube measure the amount of pressure generated when the muscles of the stomach and intestine contract and squeeze tightly around the tube. The greater the contraction of the muscles, the greater the pressure sensed by the tube. Contractions are recorded at rest for up to several hours and for one or two hours after a meal. Other contemplated tests to study patient outcomes include upper gastrointestinal x-rays, gastric emptying breath tests, and electrogastrograms.

Patient outcomes may also be tested by health-related quality of life (HRQL) measures, which extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

For purposes of this invention, beneficial or desired clinical results include, but are not limited to, alleviation of symptoms, alleviation of pain, diminishment of extent of disease, stabilized (i.e., not worsening) state of disease, delay or slowing of disease progression, amelioration or palliation of the disease state, and remission (whether partial or total), whether objective or subjective.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Chronically Implanted Electrodes at Acupoints

The feasibility study was performed in 9 regular rats and 3 diet induced obese (DIO) rats. Under anesthesia, the skin above the ST36 point was cut open slightly. The isolation of the tip end of a cardiac pacing wire (5 mm in length, serving as stimulation electrode) was peeled and the entire 5 mm exposed wire was inserted straightly into the acupoint under the assistance of a guide needle (26 gauge). The connecting isolated wire was first fixed on the muscle layer by a purse sting suture and then tunneled subcutaneously to and exited at the back of the neck. The placement of electrodes at the bilateral was the same. After both electrodes are placed, the cut-open skin above the acupoints was closed with sutures. The rats were housed in the regular cage and given regular food/water, and observed for a period of 2 weeks. The proper placement of electrodes after two weeks was confirmed by the measurement of impedance below 1500Ω and by electrical stimulation via the implanted electrodes: slight muscle contractions were noted at the acupoint when electrical current was delivered similar to EA with the insertion of a needle. No adverse events or unusual behaviors were observed during the two-week period. Two weeks later, the animals were sacrificed under anesthesia and the skin above ST36 was cut open and the placement of the electrodes was visually examined. No displacement or inflammation was noted.

Figure 7:
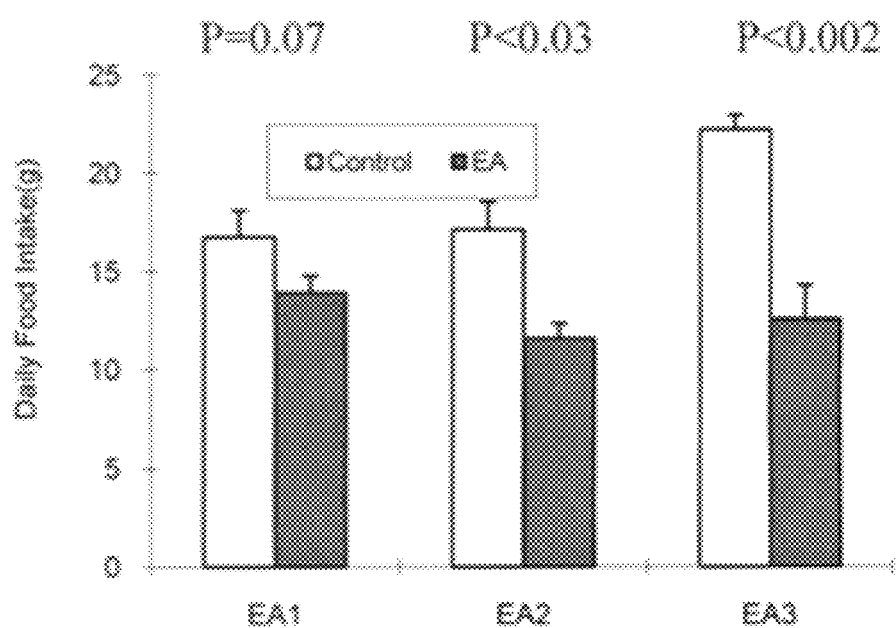
FIG. 7 provides an illustration of how electrostimulation at given stomach meridians affects food intake.

The efficacy study on food intake was performed in 6 of the regular rats. After acclimation to 2 hrs/day food intake, the animals were subjected to a three 2×2 crossover study (1st 2 weeks (wk): crossover for control and EA 1; 2nd wk: crossover for control and EA2; 3rd wk: crossover for control and EA3). The daily food intake during these 4 treatment regimens is presented in FIG. 7 and it is seen that while all methods of EA reduced food intake in comparison with the control (no EA), EA3 (0.5 ms, 15 Hz, 10 mA) was more potent than EA2 (0.5 ms, 15 Hz, 6 mA) and EA1 (0.5 ms, 15 Hz, 6 mA, 2 s-on and 3 s-off). It can also be noted that the animals ate more (during control) in the 3rd test period than the 1st test period because they were growing and got bigger.

From the above studies, the following has been observed: daily EA during feeding using chronically implanted electrodes significantly reduces food intake in both regular and DIO rats; chronic EA using implanted electrodes at ST36 is feasible and does not cause adverse reactions; and the impedance is substantially lower when the electrodes are placed at ST36; the measure may be used to accurately place electrodes at acupoints.

Example 2

EA Effects on Glucose

Electroacupuncture via chronically implanted electrodes has a hypoglycemic effect in rodent models of diabetes. Stimulation electrodes were chronically implanted at acupoints (CV 12 and CV 14) in regular (N=6), diet-induced obese (DIO, N=12), and Zucker diabetic fatty (ZDF, N=8) rats. The oral glucose tolerance test (OGTT) was performed in conscious state with EA and sham-EA with following parameters: A: train-on of 2 s, train-off of 3 s, 0.5 ms, 15 Hz, 6 mA; B: same as A except 10 mA. It was found that: (1) In regular rats, the blood glucose increase after oral glucose was not altered with EA of parameter A, but was attenuated with EA of parameter B (60% vs. 44%, P=0.03). 2). EA of parameter B also attenuated the postprandial glucose increase in both DIO rats (47% vs. 35%, P=0.005) and ZDF rat (152% vs. 132%, P=0.02). These data suggest that EA can reduce postprandial glycemia in obese and diabetic rats.

Example 3

EA Effects on Insulin Resistance

Electroacupuncture improves high fat diet-induced insulin resistance (IR) in mice. Intraperitoneal Glucose Tolerance Testing (IPGTT) and Insulin Tolerance Testing (ITT) were preformed in control mice fed with regular chow (N=6) and mice fed with high-fat diet (N=6) with sham-EA (no stimulation) or EA via needles inserted at CV4 and CV 12. It was found: (1). The glucose level in the high fat diet group was higher than the control mice at baseline (186.5±20 mg/dl vs. 259.8 ±13 mg/dl) and every time point after glucose injection (348.5±18.9 vs. 429.5±28.3 mg/dl at 30 min, 307.2±9.2 vs. 481.3±14.5 mg/dl at 90 min, all P<0.05). (2). EA at CV4 and CV12 reduced postprandial glucose level in the high fat diet mice. The absolute % change of glucose was reduced by 38% at 90 min and 42% at 120 min with EA (P=0.03 vs. sham-EA. (3). EA increased the insulin sensitivity in the high fat diet mice. The absolute % change of glucose in the ITT was reduced by 34% at 15 min, 68% at 60 min and 71% at 120 min (all P<0.02) with EA.

Example 4

EA Effects on Emesis

Electroacupuncture via chronically implanted electrodes reduces cisplatin-induced emesis.

Methods: Adult male Sprague Dawley® rats were adapted to be single-housed in wire bottom cages with access to food, kaolin, and water from 6:00 PM-10:00 AM daily. Rats were randomized to receive intraperitoneal injection with either saline (n=3) or cisplatin 6-10 mg/Kg). Daily kaolin intake was observed for 30 days. Rats underwent EA surgery for the placement of 2 pairs of electrodes at bilateral PC6 and ST36 acupoints. Following recovery, rats underwent 3 days of 1-3 hour adaptation in Bollman's cages. While restrained, rats received either Sham EA (electrodes implanted but no stimulation was given) or EA (on bilateral PC6 and ST36) for 2 successive days, each. The frequency of EA was either 10 or 20 Hz, and its duration lasted for 1 or 3 hours. Pulse width was maintained at 0.6 ms and its amplitude was from (0.4-2.0 mA). Following sham EA or EA, rats were placed in the wire bottom cages with access to food, kaolin and water. Average kaolin intake was observed for the following 24 hrs after sham EA or EA for 2 consecutive days.

Results: (1) Cisplatin treatment increased kaolin intake exponentially over 30 days: 0.01±0.0; 0.19±0.1; 1.70±0.5; 2.88±0.5 and 3.73±0.5 for pre-treatment day 1 and post treatment days 1, 10, 20 and 30, respectively (p≤0.01 for each vs. pre-treatment intake). In contrast, saline-treated rats hardly ate any kaolin: intake varied from 0.00-0.06 g at all times. (2) EA with 10 Hz frequency was effective in reducing kaolin intake when given for 3 hrs, not 1 hour; while EA with 20 Hz frequency was effective when given for 1 or 3 hrs (see table 1).

Conclusion: Chronic EA is effective in reducing pica in a rodent model of CINV.

TABLE 1

| EA Parameters | Kaolin intake | | P value (t-test) |
| --- | --- | --- | --- |
| | Sham EA | EA | |
| 10 Hz for 1 hr (n = 7) | 4.16 ± 1.1 | 4.28 ± 1.2 | 0.4 |
| 10 Hz for 3 hrs (n = 6) | 5.73 ± 0.9 | 3.33 ± 0.7 | 0.0004 |
| 20 Hz for 1 hr (n = 7) | 5.86 ± 0.9 | 3.88 ± 0.6 | 0.007 |
| 20 Hz for 3 hrs (n = 8) | 5.51 ± 1.1 | 3.08 ± 0.6 | 0.005 |

Example 5

Synchronized Electroacupuncture

In addition to regular EA, there is a biofeedback system to synchronize a subject's breathing according to the stimulation frequency (trains/min) of the pulse generator such that vagal activity is increased. The system is composed of the following: an ECG amplifier, a microstimulator, a software algorithm to derive an heart rate variability (HRV) signal from the ECG and to calculate power spectrum of the HRV signal, and a biofeedback system. A special software package is used and composed of followings: (1) an HRV system. The ECG signal from the amplifier is processed for the detection of R-R intervals and an HRV signal is displayed; 2) a biofeedback training system that displays two signals: (a) the HRV signal obtained from the subject and (b) a sinusoidal wave generated based on the frequency (trains/min) of the stimulator output that is used as a target. The subject is asked to breathe in whenever electrical stimulation is sensed and to breathe in such a way that the HRV signal displayed on the PC is as closely matched to the target signal as possible.

A study has been performed in 6 healthy volunteers to test the hypothesis that SEA is more effective than EA in enhancing vagal tone. Each subject underwent two sessions. In one session, the ECG was recorded at baseline and during the conventional EA; the protocol of the second session was the same except EA was replaced by SEA that was performed by setting the frequency at a rate of 10-12 trains/min, dependent on subjects, and asking the subject to breathe in whenever he/she sensed electrical stimulation. SEA was performed using a microstimulator via bilateral ST36 using the following parameters: train-on of 2 s, train-off of 4 s, pulse frequency of 25 Hz, width of 0.5 ms, amplitude of 2-6 mA (depending on the sensation of the subject: felt tolerable sensation). In comparison with baseline, vagal activity (HF) was significantly increased with SEA (0.32±0.05 vs. 0.60±0.07, P=0.025, almost a 100% increase) but not with EA (0.46±0.07 vs. 0.45±0.09, P=0.4). Concurrently, SEA but not EA reduced sympathetic activity from 0.68±0.05 to 0.40±0.07 (P<0.03), and the sympathovagal balance from 2.70±0.80 to 0.80±0.20 (P=0.05). The variation in heart rate is relatively irregular at baseline and during EA but regular and "sinusoidal" during SEA. From this study the inventors learned that conventional EA does not improve vagal tone under normal conditions although it has been shown to increase vagal activity in various disease models.

The invention claimed is:

1. A method of reducing food intake in a subject using an implantable electrical stimulation system comprising:
permanently implanting a stimulation electrode at a first location, wherein the stimulation electrode is in communication with a stomach acupoint;
permanently implanting a signal generator at a second location and connecting the stimulation electrode and the signal generator using a connector; and
reducing food intake by stimulating the stomach acupoint in the subject in need of a reduced food intake via the implanted stimulation electrode that is in communication with the stomach acupoint and coupled to the permanently implanted signal generator, wherein stimulating the acupoint reduces the subject's food intake.

2. The method of claim 1 wherein the electrical stimulation system delivers pulses on a substantially continuous basis.

3. The method of claim 1, wherein the electrical signal is a pulse train of 0.1-2 seconds on and 0.1-3 seconds off.

4. The method of claim 3, wherein the pulse train comprises a pulse of 0.1 to 1 ms.

5. The method of claim 3, wherein the pulse train comprises a pulse of 1-300 Hz.

6. The method of claim 3, wherein the pulse train comprises a pulse of 0.1 to 10 mA.

7. The method of claim 1, wherein the stomach acupoint is Zusanli (ST 36), Liangmen (ST21), or Tianshu (ST25).

8. The method of claim 7 further comprising stimulating one or more of Neiguan (PC6), Guangyaun (R4), and Quchi (LI11).

9. The method of claim 7 wherein the stomach acupoint is Zusanli (ST36).

10. The method of claim 1 wherein the stimulation electrode comprises an implantable needle.

11. The method of claim 1 wherein the stimulation electrode comprises a percutaneous lead, a paddle lead or a patch electrode.

12. The method of claim 1, wherein stimulation is electrical.

13. The method of claim 1, wherein stimulation is magnetic.

14. The method of claim 1, wherein stimulation is microwave.

15. The method of claim 1, wherein the stimulatory signal is synchronized in response to the subject's breathing.

16. The method of claim 1, wherein breathing is synchronized in response to the stimulatory signal.

17. A method of treating diabetes or obesity in a subject using an implantable electrical stimulation system comprising:
stimulating a permanently implanted stimulation electrode that is in communication with one or more stomach acupoints in a subject that is diabetic or obese selected from the group consisting of Zusanli (ST 36), Liangmen (ST21), Tianshu (ST25), Zhong Wan (CV4) and Guanyuan (CV 12) and is coupled to a permanently implanted signal generator positioned at a location other than the acupoint;
wherein stimulating the stimulation electrode treats diabetes or obesity.

18. The method of claim 1, wherein the signal generator is implanted in the subject's abdomen.

* * * * *